(12) United States Patent
Archibeque

(10) Patent No.: US 7,310,846 B1
(45) Date of Patent: Dec. 25, 2007

(54) TOOTHBRUSH AND TONGUE CLEANER COMBINATION

(76) Inventor: Eleanor D. Archibeque, 25026 Avenue 18, Madera, CA (US) 93638

( * ) Notice: Subject to any disclaimer, the term of this patent is extended or adjusted under 35 U.S.C. 154(b) by 0 days.

(21) Appl. No.: 11/510,915

(22) Filed: Aug. 28, 2006

(51) Int. Cl.
*A46B 9/04* (2006.01)
(52) U.S. Cl. .............................. 15/106; 15/110; 15/184
(58) Field of Classification Search .................. 15/106, 15/167.1, 110, 111, 184, 185, 114; 132/328, 132/308, 309–311; 601/139, 141
See application file for complete search history.

(56) References Cited

U.S. PATENT DOCUMENTS

| D243,422 S | 2/1977 | Varga |
|---|---|---|
| 5,005,246 A | 4/1991 | Yen-Hui |
| D345,055 S | 3/1994 | Boodhram |
| 5,530,981 A | 7/1996 | Chen |
| 5,709,004 A | 1/1998 | Paduano et al. |
| 5,758,380 A | 6/1998 | Vrignaud |
| 6,792,642 B2 | 9/2004 | Wagstaff |
| 6,895,624 B2 | 5/2005 | Fischer et al. |
| 2001/0054211 A1* | 12/2001 | Cabedo-Deslierres et al. ............... 15/106 |
| 2004/0134008 A1 | 7/2004 | Pham |

FOREIGN PATENT DOCUMENTS

JP 2004041260 A * 2/2004

* cited by examiner

*Primary Examiner*—Shay Karls
(74) *Attorney, Agent, or Firm*—Lawrence J. Gibney, Jr.

(57) ABSTRACT

This is a toothbrush and tongue and mouth cleaner combination, which allows an individual to brush his teeth as well as clean the interior of the mouth, using soft bristles and sponge material. The sponge and soft bristles will be placed inside the interior of a cavity in the handle and operate independently of each other.

1 Claim, 3 Drawing Sheets

TOOTHBRUSH AND TONGUE CLEANER COMBINATION

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

This relates to teeth and mouth cleaning and toothbrushes in general. With this device the teeth may be cleaned as well as the other areas of the mouth, including the tongue.

B. Prior Art

There are many other prior art references to cleaning devices for the teeth and mouth and also many other prior art references to a tongue and teeth cleaning brush combination. Representative examples of them in the prior art include Boodhram, U.S. D345,055, Varga, U.S. D243,422 that is a tongue brush design and Paduano, U.S. Pat. No. 5,709,004. Paduano is a device with toothbrush bristles on one end and a tongue scraper on the other. Another example includes Yen-Hui, U.S. Pat. No. 5,005,246.

While the prior art references are very similar in terms of scope and function, the structure is completely different in this particular application.

BRIEF SUMMARY OF THE INVENTION

This is a combination toothbrush, tongue and mouth cleaner. It will have the appearance of a normal toothbrush with a handle and toothbrush bristles on one end. On the side opposite the toothbrush bristles will be a track. This track will allow a sponge and a soft bristle mouth cleaner to be deployed when necessary. The sponge and soft bristle mouth cleaner will operate independently of each other. The sponge and soft bristle mouth cleaner will be encased in the top portion of the handle, which is partially hollow.

The sponge and the soft bristles operate independently of each other, using different slider buttons on the side. The slider button will be in a track and will retract the sponge and soft bristle mechanisms independently.

It is an object of this device to construct a device, which will operate as a toothbrush but also allow the user to clean his or her tongue and other portions of the mouth with a sponge or soft bristles.

DETAILED DESCRIPTION OF THE EMBODIMENTS

Figure 1:
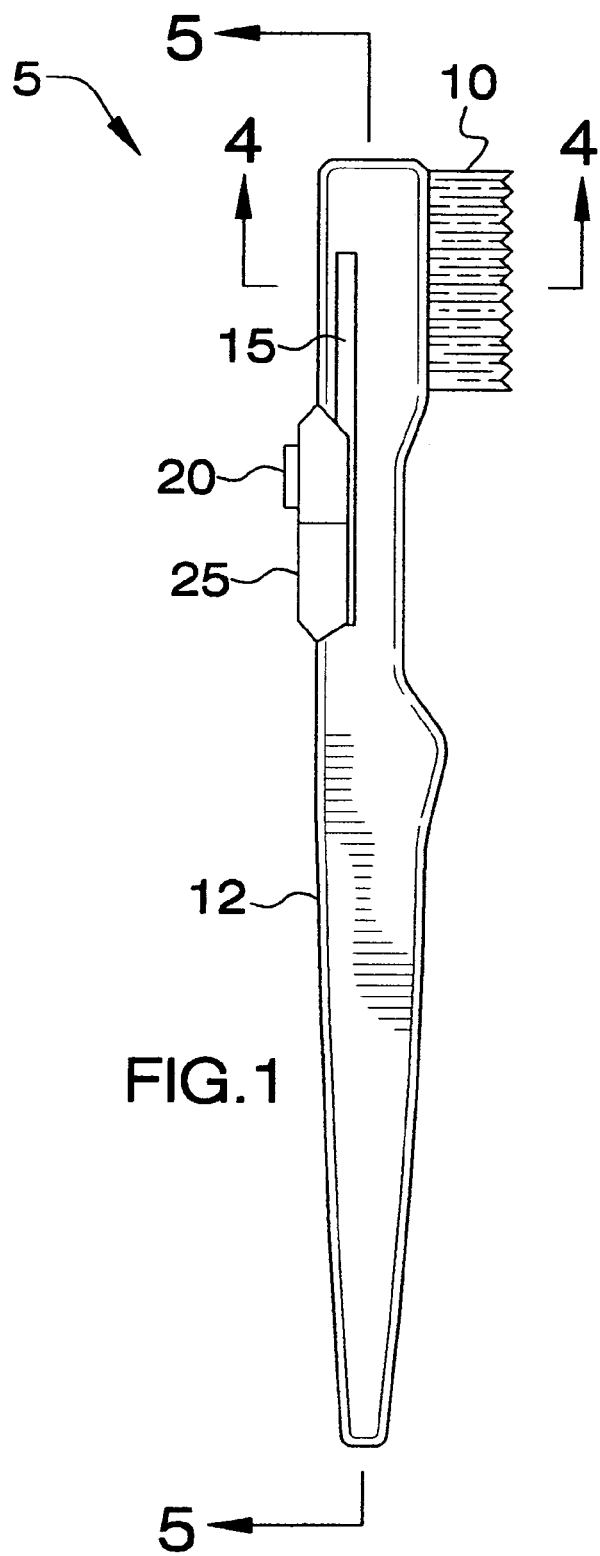
FIG. 1 is a side view of the device.
Figure 2:
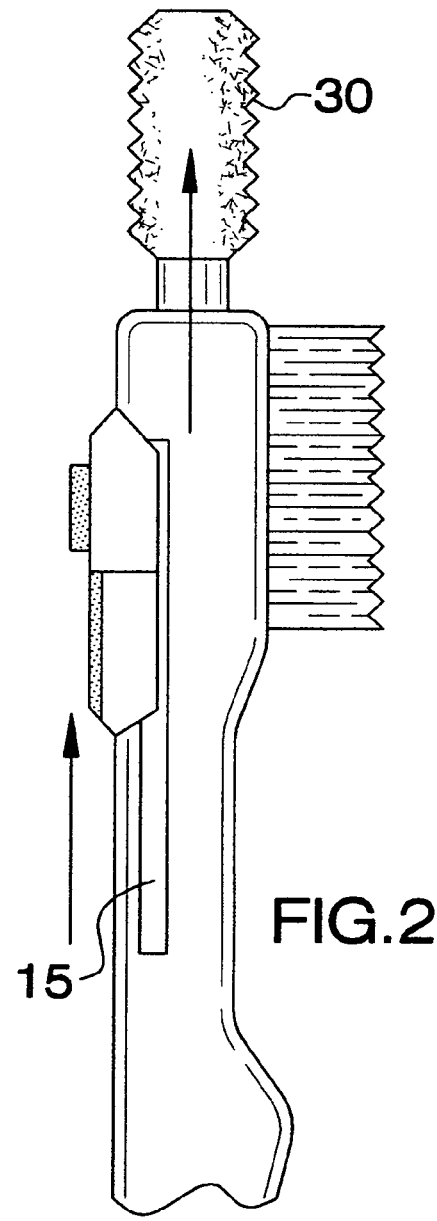
FIG. 2 is a partially fragmented view on the side with the soft bristles in the extended position.
Figure 3:
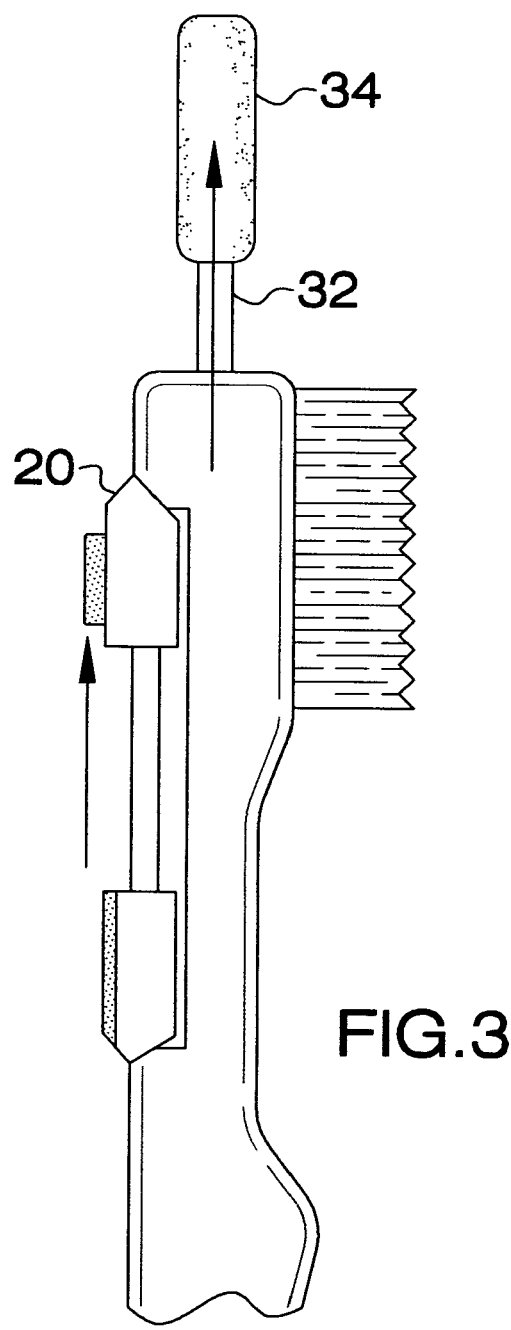
FIG. 3 is a partially fragmented side view of the sponge extended.
Figure 4:
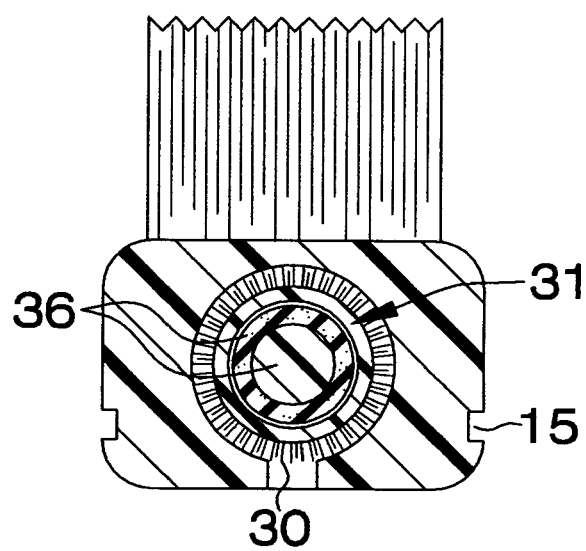
FIG. 4 is a view according to line 4-4 on FIG. 1.
Figure 5:
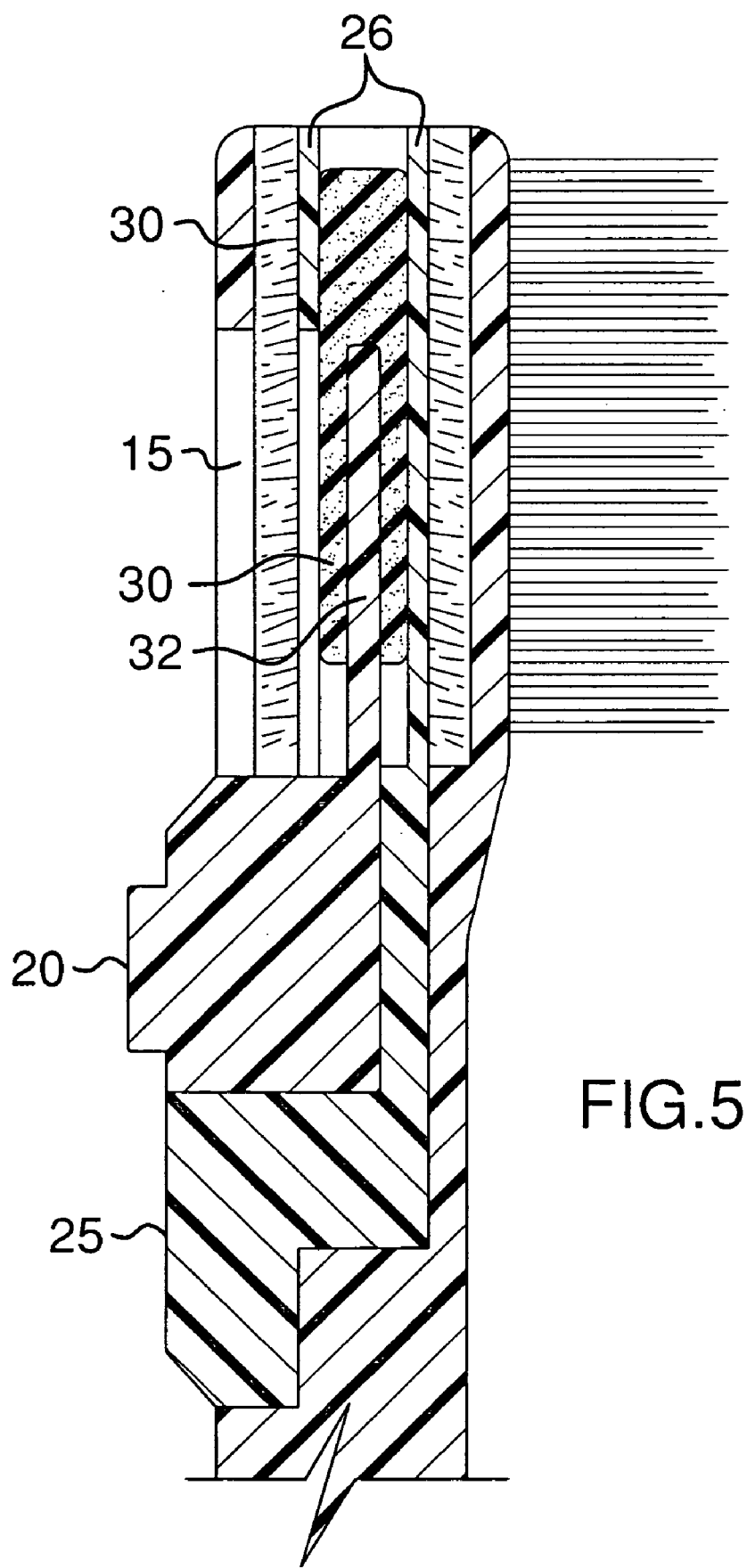
FIG. 5 is a cross-sectional view according to line 5-5 on FIG. 1.

This device 5 is a standard toothbrush with toothbrush bristles 10 and a handle 12. Unique to this particular construction, however, and located in the interior of portion of the hollow handle 12 is a sponge 34 as well as soft bristles 30.

On the side opposite the toothbrush bristles will be the hollow portion of the handle and track 15 with two slider buttons and a sponge slider button 20 and a bristle slider button 25. By moving the respective slider button up and down, it will allow the sponge 34 or bristles 30 to be exposed above the top surface of the handle. Both the sponge 34 and the soft bristles can be retracted inside the handle 12 by simply moving the appropriate slider button. The sponge and soft bristle cleaning devices operate independent of each other on this device.

The device may be constructed of material that is commonly used with toothbrushes.

While the embodiments of the invention have been disclosed, certain modifications may be made by those skilled in the art to modify the invention without departing from the spirit of the invention.

The inventor claims:

1. A toothbrush and tongue scraper combination, which is comprised of:
   a. a toothbrush;
      wherein the toothbrush has a handle;
      the handle is partially hollow;
      wherein the toothbrush has toothbrush bristles at a first end of the toothbrush;
   b. a single track;
      wherein the track is positioned opposite from the toothbrush bristles near a top of the first end of the handle;
      said track is positioned in the partially hollow portion of the handle;
      wherein a first button is linearly aligned with a second button along a longitudinal axis of the handle, and the first and second button are connected to the track to deploy a sponge cleaning device and a soft bristle cleaning device from the first end of the toothbrush;
   c. the sponge cleaning device is placed inside the partially hollow portion of the handle;
      wherein the sponge is connected to the first button that slides within the track;
   d. the soft bristle cleaning device is placed in the same partially hollow portion of the handle as the sponge cleaning device;
      wherein the soft bristle cleaning device is connected to the second button that slides within the track;
      wherein the soft bristle cleaning device encases the sponge cleaning device;
      wherein the sponge cleaning device and soft bristle cleaning device can be operated independently from each other;
      wherein the sponge cleaning device can be replaced;
      wherein the soft bristle cleaning device can be replaced.

* * * * *